United States Patent [19]

Scharf

[11] Patent Number: 4,467,085
[45] Date of Patent: Aug. 21, 1984

[54] CHEMICAL COMPOUNDS, PROCESS FOR THEIR PREPARATION, AGENTS CONTAINING THESE COMPOUNDS, AND THEIR USE

[75] Inventor: Gerhard Scharf, Hoechst Aktiengesellschaft, D-6230 Frankfurt am Main 80, Fed. Rep. of Germany

[73] Assignee: Gerhard Scharf, Fed. Rep. of Germany

[21] Appl. No.: 258,408

[22] Filed: Apr. 28, 1981

[30] Foreign Application Priority Data

Apr. 30, 1980 [DE] Fed. Rep. of Germany ....... 3016618

[51] Int. Cl.$^3$ .......................... C12Q 1/26; C12Q 1/28; C12Q 1/54; C08B 11/00
[52] U.S. Cl. ...................................... 536/43; 436/95; 436/164; 436/166
[58] Field of Search .......................... 536/43; 435/805

[56] References Cited

U.S. PATENT DOCUMENTS

| | | | |
|---|---|---|---|
| 2,905,594 | 9/1959 | Morris | 435/805 |
| 3,388,118 | 6/1968 | Tesoro | 536/43 |
| 3,616,251 | 10/1971 | Lin | 435/805 |
| 3,823,100 | 7/1974 | Rothwell et al. | 536/43 |
| 4,109,080 | 8/1978 | Lieser et al. | 536/43 |
| 4,224,439 | 9/1980 | Ayers et al. | 536/43 |
| 4,340,669 | 7/1982 | Bauer | 435/805 |
| 4,353,984 | 10/1982 | Yamada et al. | 435/805 |

Primary Examiner—Ronald W. Griffin
Attorney, Agent, or Firm—Curtis, Morris & Safford

[57] ABSTRACT

Carrier-bonded compounds are described which serve as chromogens for analytical indicators contained in a carrier. A process for the preparation of these carrier-bonded chromogens, an agent containing these chromogens, and their use in the detection and determination of constituents of body fluids and excrements are also described.

12 Claims, 3 Drawing Figures

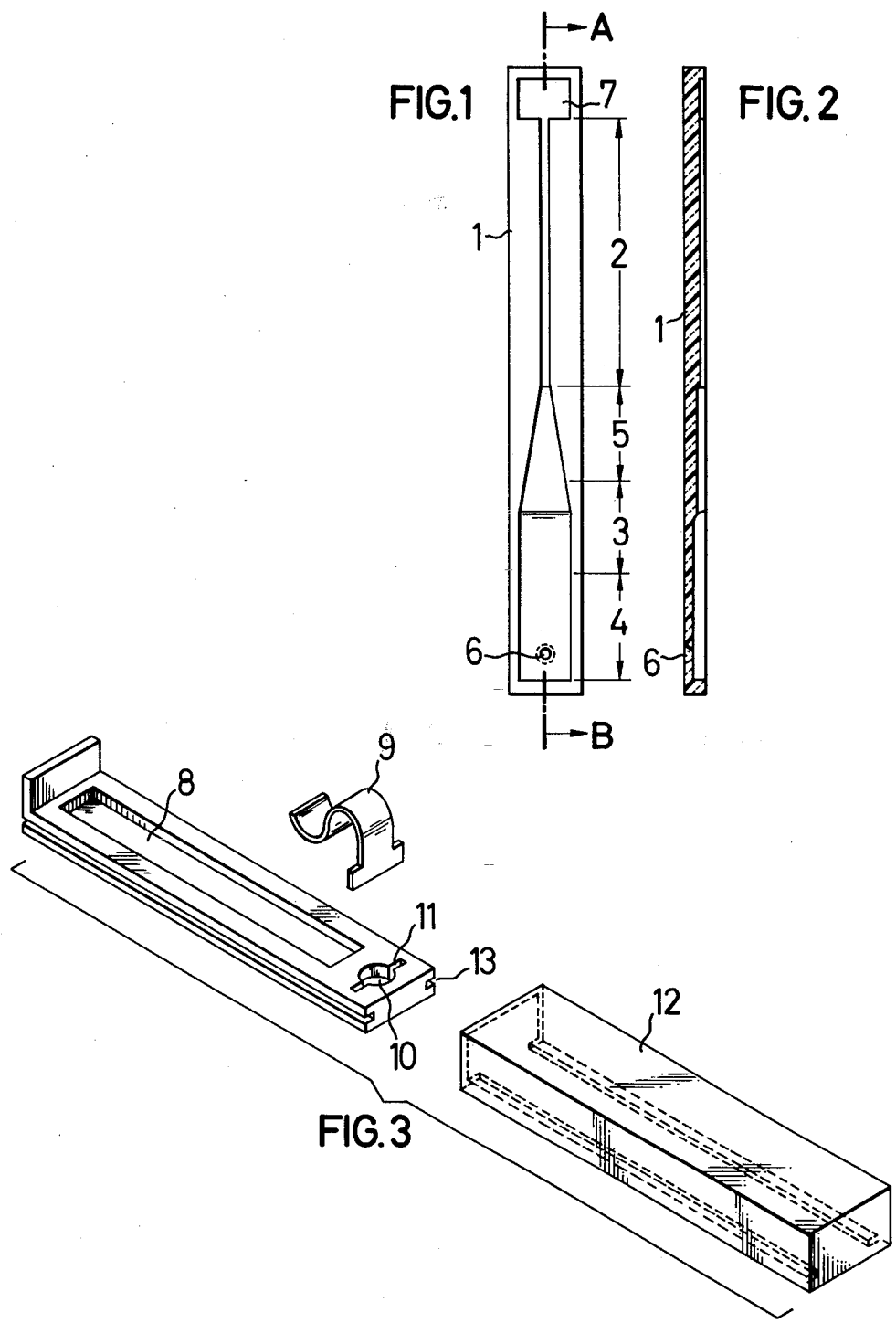

CHEMICAL COMPOUNDS, PROCESS FOR THEIR PREPARATION, AGENTS CONTAINING THESE COMPOUNDS, AND THEIR USE

The invention relates to carrier-bonded compounds which serve as chromogens for analytical indicators contained in a carrier, to a process for their preparation, to agents containing these compounds, and to their use in the detection and determination of constituents of body fluids or excrements.

In such detection and determination processes, agents referred to as test strips are nowadays used, for simplicity. Such agents are described, for example, in German Offenlegungsschrift No. 2,922,856.

A problem which can arise when using such test strip systems is that the indicators formed in the test reactions can "bleed", and as a result the indication is not sharp and there is a loss in accuracy of the test result. Solutions to this problem have already been proposed, but are not devoid of disadvantages.

It has now been found that it is advantageous to use indicators which are prevented from diffusion in the carrier by being bonded, preferably covalently bonded, to a carrier material, such indicators preferably being chromogens from which dyestuffs are formed in the course of the test reaction.

It was known that, in test tubes for the determination of ions, complexing agents serving as indicators can be ionically bonded to carriers (Labor Praxis 1980, No. 3, pages 26–29).

It was also known to employ agents for the detection and determination of glucose in liquid containing glucose, involving the catalytic oxidation of the glucose and formation of hydrogen peroxide. The determination of the concentration or amount of the hydrogen peroxide formed can serve to quantify the substrate concentration or amount. For this purpose, the oxidation of suitable chromogens, catalyzed by the enzyme peroxidase, can be utilized. The use of test strips in this context is particularly simple. The information given by the test is based on the information concerning the dyestuff concentration which is formed within a finite period of time and which can be determined either subjectively by comparison with a color scale or objectively by the use of a reflection photometer. Suitable chromogens are known. However, at least in the case of the subjective evaluation, the result can be best be described as semi-quantitative.

In test agents for semi-quantitative or quantitative indication it is alternatively possible to utilize the length of a colored zone formed, after applying a defined amount of test substance, as a measure of the substance concentration or amount.

This presents the problem that the indicator layer formed can be partially dissolved by the solvent flowing through the indicator and then, as is known in the case of all chromatographic processes, travels in the direction of the mobile phase; for this reason, in test tubes for the quantitative determination of ions (Labor Praxis 1980, No. 3, pages 26–29, Vogel-Verlag, Würzburg) the complexing agents which act as indicators are ionically bonded to cellulose ion exchangers which serve as fixed carriers. Since the total charge of the complexing agent after reaction with the ion to be investigated is unchanged, the affinity of the indicator to the cellulose matrix does not change significantly and the indicator zone formed undergoes virtually no migration on passage of excess solvent. To achieve this, however, the ionic strength of the mobile phase must be kept low.

However, at least the test liquid itself contains foreign ions which cause certain ion exchange effects to occur with the indicator on the cellulose matrix. This effect is intensified if substantial amounts of mobile phase are passing through, since, in order to maintain the desired reaction conditions, it is often necessary to maintain a certain pH range, for which purpose electrolytes must be employed as buffer substances. The consequence of these effects is that the boundary of the colored zone formed is not sharply marked and shifts in the direction of travel of the mobile phase as more of the latter passes through.

The principle of the formation of colored zones whose length is a measure of the concentration or amount of a substance, requiring analysis, in a test liquid which has been applied to the agent has also been tried out for the analysis of sugars.

The procedure there proposed, however, has the effect that the hydrogen peroxide formed in the reaction zone remains free in solution, at least for a few minutes, without undergoing a secondary reaction. Under these conditions, the enzyme catalase present in virtually all glucose oxidase preparations can consume hydrogen peroxide to an indeterminate extent.

The main objective of the procedure, namely the formation of a colored zone whose length is a measure of the amount of glucose applied, therefore appears unattainable with the agents mentioned.

In German Offenlegungsschrift No. 2,922,856, referred to above, the indicator zone is impregnated with a solution of a chromogen, preferably o-tolidine. Here, both the chromogen and the dyestuff formed are substances which are to some extent soluble in water. As a result, both the chromogen and the dyestuff formed after the oxidation can travel with the aqueous solution which ascends during use. We have found that a color spot of tolidine which has been oxidized to a green dyestuff, at concentrations of tolidine and glucose which are comparable to those in the above Offenlegungsschrift, will, at pH 6 and a migration distance of the mobile phase front of 32 mm, travel with the mobile phase, with a diffuse front, for between 4 and 9 mm, depending on the speed of migration of the mobile phase. Accordingly, with the procedure which has been proposed, an exact and reproducible boundary between the converted and unconverted areas of the indicator zones cannot develop.

It has been proposed that this shortcoming, evidently also recognized by the Applicant, should be reduced by applying the indicator in streaks, between which there can be substances which bond the dyestuff.

The objective of the formation of an exactly bounded, uniformly reacted color zone which is proportional to the amount of substance applied and consists of a chromogen converted to a defined reaction product, with the dyestuff formed being non-diffusing, is not attainable with the methods hitherto proposed.

It is therefore the object of the present invention to immobilize the chromogens used without losing their ability to function as the substrate for the hydrogen peroxide/peroxidase system.

The invention relates to a process for the preparation of compounds, bonded to a carrier, to serve as chromogens for analytical indicators contained in a carrier, which process comprises bonding a chromogenic compound, where appropriate covalently, to a carrier, where appropriate via an intermediate compound which modifies the distance between the chromogenic compound and the carrier.

The invention further relates to a diagnostic agent which consists of a strip-shaped carrier containing the chemicals required for the test reaction, and wherein the chromogen and indicator molecule are bonded to an insoluble carrier material.

The invention yet further relates to a process for the preparation of such an agent and to the use of a chromogen and indicator, bonded to an insoluble carrier material, in such an agent.

A better understanding of the invention will be had by referring to the accompanying drawings wherein FIG. 1 is a plan view of a diagnostic agent according to the present invention in the form of a test stick;

FIG. 2 is a side view of the test stick of FIG. 1 taken along line A-B; and

FIG. 3 is a perspective view of a device for use with a test stick as shown in FIG. 1.

A more complete description of the drawings is found below in Example 1 of the application.

Preferred agents are those whose use results, by reaction of a chemical contained in this agent with a constituent of the body fluid or of the excrement, in a reaction product which penetrates into a part of the test strip referred to as the reaction zone and there modifies the properties of an indicator, especially of a chromogen, in a manner which can be evaluated.

It was not to be foreseen that the formation of ionic or covalent bonds between a carrier, such as, for example, cellulose, and a chromogen would not destroy the substrate function of the latter in respect of the system hydrogen peroxide/peroxidase.

The range of usable chromogens comprises virtually all chromogens hitherto used, but also substances which, whilst they react with the hydrogen peroxide/peroxidase system, and thereby undergo a color change, have hitherto not been used, for reasons of stability or of intrinsic color of the chromogen in the reduced state. In addition, novel chromogens, which have not hitherto been used, can also be employed.

We have found that to produce the chromogencarrier bond, numerous possible ways of producing bonds can in principle be employed, for example alkylations between haloalkyl or oxirane groups, fixed to the carrier, and chromogens which contain amino, hydroxyl or sulfhydryl groups. It is also possible to produce ester or thioester bonds between chromogens containing carboxyl groups, and hydroxyl or sulfhydryl groups on the carrier.

The last two types of bonds were achieved, for example, by treating cellulose, containing hydroxyalkyl or sulfhydryl groups, by means of the carbodiimide method (Chem. Rev. (1967) 67, 107). Using this method, it is also possible to produce amide bonds either between chromogens containing carboxyl groups and carriers containing amino groups or conversely between chromogens containing amino groups and carriers containing carboxyl groups. Furthermore, using this method, ether bonds and thioether bonds can be produced in the case of chromogens containing hydroxyl or sulfhydryl groups.

Further, chromogens bonded to polymers have been obtained by coupling reactions. In these cases, it has generally proved advantageous to fix the chromogen, to be bonded, at a sufficiently large distance from the matrix of the polymer as, for example, in the carrier-bonded chromogen of the formula I.

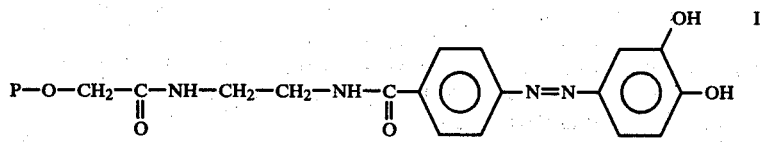

P=polymer.

Compound I is a yellow powder which, compared with pure pyrocatechol, exhibits greater stability to oxidation in air or in aqueous solution.

Suitable polymers are especially those which carry hydroxyl groups, and in particular cellulose.

It has been observed, as a quite general rule, that the sensitivity to oxidation is reduced by producing a bond to a carrier. For example, o-dianisidine which has been bonded to cellulose by means of bromoacetyl groups shows no perceptible auto-oxidation after more than three years in air. Representatives of the benzidine series have been preferred for use as chromogens, the compounds being bonded to the carrier, preferably cellulose, via long-chain spacers. These substances are very stable to oxidation in air. On the other hand, they can be directly oxidized enzymatically at comparably high rate to that of the non-bonded compounds.

Adequate stability in the moist state is on the other hand dependent on the observation of certain conditions. Wetted with distilled water, most of the polymer-bonded chromogens used prove completely stable for several days. The stability diminishes as a result of the presence of certain ions, and many divalent cations, but especially Fe(III) ions, catalyze the oxidation of moist chromogens. Some anions, in the main polyvalent anions, also have a similar effect.

These properties in turn affect the choice of suitable buffer systems. For example, the o-dianisidine preparation described in Example 1, at a pH of about 4 in an acetate buffer, hardly undergoes any auto-catalytic oxidation, whilst it undergoes more pronounced auto-catalytic oxidation in a citrate buffer.

This results in considerable differences within the class of substances used preferentially.

The sensitivity to oxidation of polymer-bonded tolidine is particularly high. At pH values of 4-5, tolidine bonded via a spacer visibly turns blue within a few minutes in the presence of peroxidase, this color change possibly also being assisted by iron ions which issue, in traces, from the enzyme preparation. Polymer-bonded o-dianisidine has better stability.

The stability can be further improved by secondary reactions of the polymer-bonded chromogens P—OCH₂CH(OH)CH₂O(CH₂)₄OCH₂CH(OH)CH₂NH 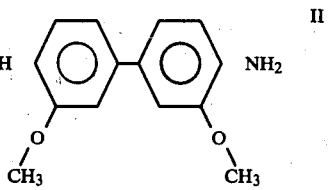 NH₂

II

P=polymer

Whilst the polymer-bonded o-dianisidine shown in formula II already possesses adequate stability, a secondary reaction with stoichiometric amounts of 2-chloroethanol and tri-n-butylamine in dimethylformamide gives a preparation which, when used in test sticks, shows no detectable auto-oxidation above the color zone formed. The category of substances used preferentially comprises multi-stage redox systems. Because the present problem demands a stoichiometric reaction, the formation of a defined oxidation product is desirable.

The chromogens of the benzidine category, polymer-bonded via a spacer, mostly react at low pH values to give intensely colored intermediates in the gree-blue color region. At pH values of about 7, on the other hand, the next-higher oxidation stage is formed which, for example, in the case of o-anisidine lies in the region of brown color shades, for all the types of carrier bondings which have been tried.

The pH-dependent formation of the individual oxidation stages also influences the length of the strip of color formed.

Furthermore, the rate of reaction with hydrogen peroxide/peroxidase is an important parameter. The enzyme catalase contained in many commercial peroxidase preparations consumes hydrogen peroxide, and hence the amount of peroxidase should be kept as low as possible.

This problem can be circumvented if the hydrogen peroxide formed is consumed by means of an intermediate redox system which is easily oxidizable by the system hydrogen peroxide/peroxidase, and the oxidizing agent formed as an intermediate reacts with a polymer-bonded chromogen.

A water-soluble iodide can advantageously be used as the intermediate oxidizing agent.

The iodine formed from iodide by means of hydrogen peroxide/peroxidase is capable of decolorizing a range of carrier-bonded dyestuffs, for example neutral blue, gallocyanine or indigo-carmine, and can also oxidize carrier-bonded leuco dyestuffs to the corresponding dyestuffs.

Many of the directly oxidizable polymer-bonded chromogens can also be employed for this reaction.

For example, iodine reacts with o-dianisidine bonded to cellulose via a spacer, and equally with o-tolidine and benzidine, to form greenish blue dyestuffs.

To prevent oxidation of the carrier with iodine, iodine must, where necessary, be added as a complexing agent. In general, about 10% by weight, measured in terms of the amount of polymer-bonded chromogen, suffices.

For the preparation of the reaction zone of the test sticks it is essential that the enzymes peroxidase and glucose-oxidase should be immobilized. At pH values below 6 this is adequately the case merely by using a sufficiently strongly acidic cation exchanger, which has beforehand been brought to the Na⁺ or K⁺ form. Peroxidase is bonded strongly and glucose-oxidase moderately. Quaternized diethylaminocellulose also shows an immobilizing action in respect of glucose-oxidase.

In general, an addition of mutarotase is not necessary. The glucose peroxidase preparation used, though highly purified, revealed adequate mutarotase activity, so that even with an analysis time of less than 5 minutes, a uniformly colored and sharply defined color zone of reacted chromogen was obtained.

The fluid to be analyzed, for example blood or urine, can be delivered via an absorbent carrier, in which case a defined amount of substance can be applied by wetting a defined zone for a limited period of time. Membrane filters are more suitable than, for example, paper, the absorbency of which depends on the atmospheric humidity. Suitable base materials for such filters are, for example, the cellulose esters preparable by conventional procedures, especially cellulose 2.5-nitrate or cellulose acetate. If ionically bonded chromogens are used, desalination may be necessary. In a preferred embodiment, solutions of the materials, prepared in a conventional manner, are poured into the recess of the stick shown in FIGS. 1 and 2, and excess material is removed. The stick preferably is made of plastic and is provided with a longitudinal recess, which can taper. Evaporation of the solvent then results in the formation of the filter material on the bottom. At the back of the stick, a part of the area of the membrane can remain uncovered, that is to say the stick has an orifice which is closed, during coating, by means of a material, for example polyethylene or polystyrene, to which the filter material shows little adhesion.

Because of the good adhesion of the membrane filters to poly(methyl methacrylate), the latter material is preferably used as the base material for the production of test sticks.

The use of a membrane filter layer as the application zone has the following further advantages: With pore widths in the range of 0.6 to 1.5 microns, the material acts as a filter for all blood cells and the catalase is immobilized. The latter enzyme is contained in the blood cells and is liberated, for example, in the course of the hemolysis—which is virtually impossible to exclude—when whole blood is applied.

To remove interfering components, especially in the case of a urine sugar analysis, a zone of cation and anion exchangers (ie. a mixed bed) can be provided adjoining the application zone. This mixed bed can be produced from cellulose ion exchangers or from anion and cation exchangers based on crosslinked styrenedivinylbenzene products. The mixture of ion exchangers is pretreated with a buffer solution having a suitable pH value and is then applied, with or without binder, as a separate zone below the reaction zone. The ionic strength of the buffer, which enters the reaction zone, is determined by the ionic strength of the mobile phase.

In a blood sugar analysis, a pH gradient can be set up in the region of the ion exchange zone if acidic or alkaline solutions are employed, in order to precipitate interfering proteins and immobilize them.

To reduce the flow rate to values under which complete reaction of the polymer-bonded chromogens becomes possible at the rate of wetting with the mobile phase, a zone of a membrane filter material of appropriate pore width can be applied at any desired point below the reaction zone. Analogously to the determination of glucose, the test material described can be applied in the case of other substances which are substrates for enzymes which during the oxidation of the substrates produce hydrogen peroxide.

Further possible uses of carrier-bonded chromogens and indicators are accordingly, for example, the quantitative detection of cholesterol by means of cholesterol-oxidase or the quantitative detection of galactose by means of galactose-oxidase.

The examples which follow illustrate the invention.

EXAMPLE 1

Preparation of the carrier-bonded chromogen 0.5 g of cellulose powder having an average particle size of 10 microns is stirred for 20 hours at 25° C. in a mixture of 3 ml of 0.2M sodium hydroxide solution and 1.5 ml of butane-1,3-diol diglycidyl ether. The powder is then filtered off, and washed with 0.2M sodium chloride solution until a neutral filtrate is obtained. 0.5 g of o-dianisidine are dissolved in 10 ml of dimethylformamide and the solution is mixed with 10 ml of a degassed 0.2M sodium bicarbonate solution, whilst nitrogen is being passed through. The pH is brought to 10 with 2M sodium hydroxide solution and 0.5 g of polyethylene glcyol 4000 is added. The cellulose preparation is then added and the mixture is stirred for 2 hours at 80° C., whilst nitrogen is being passed through. The product is filtered off, washed repeatedly with dimethylformamide, until the filtrate is free of o-dianisidine, and is then washed repeatedly with 0.2M sodium chloride solution and with 0.5M acetic acid, twice with distilled water and twice with methanol, and is dried in air.

This product consists of o-dianisidine bonded to cellulose via a spacer. The product is a substrate for the system hydrogen peroxide/peroxidase and is oxidized by this system, in the pH range of 3.5–6, to give an intense green dyestuff. 0.2 g of this product are suspended in 5 ml of dimethylformamide, 0.0014 ml of 2-chloroethanol and 0.0095 ml of tri-n-butylamine are added, the mixture is heated for 4 hours at 100° C. whilst stirring, and the product is filtered off, washed with dimethylformamide, repeatedly with 0.2M sodium chloride solution, with distilled water and twice with methanol and is dried in air. The product obtained has all the advantages of the preceding product in respect of enzymatic oxidizability, but has greater stability to autocatalytic oxidation in air, when moist.

Coating of the test sticks (1 in FIGS. 1 and 2)

First, the solutions for coating the individual zones are prepared.

Reaction zone (2) with collecting zone (7): 0.4 g of carrier-bonded chromogen are mixed with 0.1 g of sulfoethylcellulose in the sodium form, 0.1 g of quaternized diethylaminocellulose in the chloride form and 3 ml of 0.1M dimethylglutaric acid buffer or pH 4.0.

Ion exchange zone (3): 0.05 g of an anion exchange resin containing quaternary ammonium groups (the resin being in the OH form) and 0.05 g of a cation exchange resin containing sulfonic acid groups (the resin being in the $H^+$ form), (both resins having been milled), are impregnated with 0.12 ml of 90% strength n-propanol and mixed with 0.3 ml of a membrane filter solution which is as described as below (see application zone), but has a higher water content.

Applicaton zone (4): 5 g of cellulose 2.5-nitrate are dissolved in 55 g of methyl acetate. 24 g of absolute alcohol, 12.3 g of n-butanol, 1.5 g of glycerol and 3.2 g of water are then added.

Zone for regulating the flow rate (5): A solution corresponding to that employed for the application zone can be used here. The water content of the solution determines the pore size of the filter produced after drying, and can be higher here than in the application zone.

About 30 sticks at a time are placed on a support wich possesses fittings for the orifices (6) in the sticks, and which initially masks the zones intended for coating with membrane filter material.

The reaction zone (2) is coated whilst constantly stirring the impregnating solutions.

After the solution has slightly dried, the masks are removed and the remaining zones are coated with the membrane filter solutions. These solutions gel immediately when they come into contact with barrier layers which are still moist. After drying under defined conditions, for example 70% atmospheric humidity and 25° C., the sticks are coated with enzyme solution. This can be done automatically by means of an apparatus in which a defined amount of enzyme is applied in each case by means of a wick. 2–5 micrograms of glucose-oxidase and of peroxidase (activity in each case about 250 U) suffice.

Finally, the sticks are carefully detached from the support and a paper strip with graduation can be glued to the sticks.

The membrane filter solution has solidified to constitute a filter adhering to the bottom. When applying a 1 mm thick coating, and at a water content of 3.2%, an 0.06 mm tick filter material with about 0.6 micron pore width forms. Such a filter material can be used, for example, for urine testing. For testing whole blood, the pore width is advantageously increased to values of between 1 and 2 microns by a correspondingly higher water content of the solution employed for the application zone.

The test stick, charged with the solution to be analyzed, can now, for analysis, be brought into a horizontal or slightly inclined position by means of the device shown schematically in FIG. 3. Of course, this can also be done by placing the stick in a corresponding vessel on the bottom of which there is the mobile phase.

The test stick is placed in a fit (8) of the device shown in FIG. 3. The S-shaped spring 9, provided with two holders at one of its ends, serves, after insertion of a paper strip, as a fluid transport bridge between the mobile phase reservoir 10 and the lower end of the test stick. The spring, charged with a paper strip, is pushed into the slot 11. A cover, consisting of a transparent material, is then pushed into the guide grooves 13. In doing so, the top of the cover 12 presses the spring downwards and the fluid bridge is thereby completed. At the same time, the container is sealed, and the progress of the analysis can be observed by the user.

The mobile phase, which flows successively through the zones, produces a strip of color the length of which is proportional to the amount of glucose applied.

EXAMPLE 2

Preparation of carrier-bonded p-phenylenediamine as a chromogen 10 g of cellulose powder of average particle size 10 micron are suspended overnight in 100 ml of 10% strength methanolic potassium hydroxide solution. The excess of the alkali solution is squeezed out and the alkali cellulose obtained is introduced into a solution of 8 g of chloroacetamide in 120 ml of absolute alcohol and stirred therein for one hour at 50° C.

The cellulose product is then filtered off, washed repeatedly with 0.2M sodium chloride solution until the filtrate reacts neutral, then washed repeatedly with distilled water and thereafter with methanol, and is dried in air.

The cellulose-carboxamide preparation thus obtained is introduced into 100 ml of hexamethylenediamine at 90° C. and the suspension is stirred at this temperature for 8 hours. It is then filtered hot, and the product is washed repeatedly with methanol and then with 0.2M sodium chloride solution until a neutral filtrate is obtained. Thereafter the material is washed repeatedly with distilled water and then with methanol, and is dried in air.

The product obtained contains hexylamino groups, bonded via carboxamide groups, and has a capacity of about 0.1 mole/kg.

10 g of this product are suspended in 150 ml of 0.2M sodium chloride solution and a solution of 0.4 g of p-nitrobenzoyl azide (Org. Syntheses 4, 716) in 150 ml of dimethylformamide is added. 0.17 ml of triethylamine is then added whilst stirring, and the stirring is continued for one hour. The product is filtered off, washed with dimethylformamide, 0.2M sodium chloride solution, distilled water and methanol and dried in air. The product contains p-nitrobenzoic acid hexylamide bonded via carboxamide groups.

This product is introduced into 150 ml of an 0.5M sodium bicarbonate solution. The mixture is warmed to 40° C., 5 g of sodium dithionite are added, a little at a time, whilst stirring, and the stirring is then continued at the same temperature for 30 minutes.

The product is filtered off, washed repeatedly with 0.2M sodium chloride solution, distilled water and methanol and dried in air. It contains p-aminobenzoic acid hexylamide bonded via carboxamide groups.

1 g of this product is introduced into 20 ml of an ice-cold 0.5M hydrochloric acid solution and sodium nitrite is added, a little at a time, at intervals of 3–5 minutes, until a test carried out with potassium iodide/starch paper shows excess nitrite. Stirring is then continued for 10 minutes and amidosulfuric acid is added, a little at a time, until all the excess nitrite has been destroyed.

The diazotized product is then filtered off rapidly and introduced, at a temperature of 0° C., into a solution of 2 g of p-phenylenediamine in a mixture of 50 ml of dimethylformamide and 50 ml of acetate buffer, which has been brought to a pH value of 4.2, and the batch is stirred at the same temperature for one hour.

The product is then filtered off and washed repeatedly with dimethylformamide, with dilute acetic acid solution and then with 0.2M sodium chloride solution until a neutral filtrate is obtained. The product is then washed with distilled water and methanol, and is dried in air.

The resulting slightly pinkish violet powder is the coupling product of p-phenylenediamine with the diazotized arylamino derivative of the cellulose.

This polymer-bonded derivative of p-phenylenediamine is a substrate for the system hydrogen peroxide/peroxidase and is oxidized by the latter to a brown dyestuff.

EXAMPLE 3

Preparation of carrier-bonded o-dianisidine as a chromogen 5 g of cellulose powder are treated for 1 day, at room temperature, with 12% strength methanolic potassium hydroxide solution. The alkali is squeezed out of the product and the latter is introduced, a little at a time, into a solution of 8 g of chloroacetamide in 100 ml of absolute alcohol and is stirred therein for 30 minutes at 45° C. After squeezing out, the product is washed repeatedly with absolute alcohol, with 0.2 M sodium chloride solution, with distilled water and twice with methanol and is dried in air. The cellulose-carboxamide preparation obtained is introduced into 50 ml of ethylenediamine and stirred therein for 5 hours at 90° C. Thereafter it is filtered off, washed repeatedly with methanol and then washed with 0.2 M sodium chloride solution until a neutral filtrate is obtained. The product is then washed repeatedly with distilled water and twice with methanol, and is dried in air.

The product contains ethylamino groups bonded via carboxamide groups.

1 millimole of bromoacetic acid (130 mg) and 1.1 millimoles of N-hydroxysuccinimide (127 mg) are then dissolved in 8 ml of dioxane and 1.2 millimoles (248 mg) of dicyclohexylcarbodiimide (DCC) are added as solid, and dissolved in the mixture. After one hour, the dicyclohexylurea formed is filtered off and the filtrate, which contains the ester formed from bromoacetic acid and N-hydroxysuccinimide is stirred into 42 ml of phosphate buffer, of pH 7.5, at a temperature of about 0° C. 1 g of the cellulose containing ethylamino groups is added and the mixture is stirred for 30 minutes at temperatures of about 0° C. The product is then filtered off, washed twice with a dioxane/water mixture (50/50 by volume) and then washed repeatedly with icecold 0.2 M sodium chloride solution.

The product contains bromoacetyl groups bonded to cellulose via amide bonds.

The product is immediately introduced into a solution of 3 g of o-dianisidine in 25 ml of dimethylformamide and 25 ml of 0.2 M sodium bicarbonate solution, which has been brought to a pH value of 7.8 with 2 N hydrochloric acid, whilst nitrogen is being passed through, and the mixture is heated for 2 hours at 55° C. The product is then filtered off, washed repeatedly with dimethylformamide, with 0.2 M sodium chloride solution, with distilled water and twice with methanol and is dried in air. The resulting product is a substrate for the system hydrogen peroxide/peroxidase and is oxidized by the latter, at pH values of about 7, to give a brown dyestuff.

EXAMPLE 4

Preparation of an ionically bonded chromogen 3 g of cellulose powder, in a mixture of 6 ml of 0.6 N sodium hydroxide solution, 2 ml of butane-1,3-diol diglycidyl ehter and 10 ml of water, are stirred overnight at 25° C. The product is filtered off, washed with 0.1 M sodium chloride solution until a neutral filtrate is obtained, and then washed repeatedly with distilled water and twice with methanol and dried in air. The product, which contains about 0.06 mole/kg or oxirane groups, is stirred for 2 hours in a mixture of 3 ml of N,N-diethylethylenediamine, 6 ml of distilled water and 9 ml of dimethylformamide at 70° C. It is then filtered off, washed with distilled water until a neutral filtrate is obtained and then washed twice with methanol, and is dried in air.

The resulting product contains about 0.05 mole/kg of diethylamino groups bonded via a spacer.

1.5 g of this product are stirred overnight in a mixture of 3 ml of methyl iodide and 10 ml of absolute alcohol at 40° C. The product is then filtered off, washed repeatedly with absolute alcohol, with distilled water and repeatedly with methanol and dried in air.

The product contains about 0.05 mole/kg of quaternary ammonium groups.

Benzidine-3,3-dicarboxylic acid is prepared by the method of Fierz-David and Blangey, Farbenchemie, Springer Verlag 1946, pages 157–159. Benzidine-3,3-dicarboxylic acid is a substrate for the hydrogen peroxide/peroxidase system and is oxidized by this system, at pH values of about 7, to give an intense blue dyestuff.

1 millimole (0.345 g) of benzidine-3,3-dicarboxylic acid dihydrochloride, in a mixture of 2 millimoles of 2-chloroethanol (0.135 ml) and 6 millimoles of 1,2,2,6,6-pentamethyl-piperidine (1.08 ml) in 20 ml of dimethylformamide, is stirred for 1 hour at 100° C. When the mixture has cooled, it is filtered and half the filtrate is diluted with 7 ml of distilled water and stirred for 10 minutes with 0.2 g of the cellulose ion exchanger described above. The solid is then filtered off, washed with dimethylformamide and a 50:50 ( by volume) dimethylformamide-water mixture and stirred for 10 minutes, under the same conditions, with the remainder of the filtrate. The product is then again filtered off, washed with dimethylformamide, with a 50:50 (by volume) dimethylformamide-water mixture, with distilled water and repeatedly with methanol, and is dried in air. The pale violet powder obtained is a substrate for the system hydrogen peroxide-peroxidase and is oxidized, in deionized solution, to an intense greenish black dyestuff.

This product can also be used to prepare a test stick for the quantitative detection of hydrogen peroxide or of a substance which constitutes an enzymesubstrate system which reacts to form hydrogen peroxide.

For this purpose, the ion exchange zone described in Example 1 can be coated with cation exchangers in the H+ form and anion exchangers in the OH− form. The reaction zone and detection zone can contain, in addition to the polymeric chromogen, cation exchangers in the H+ form (for example carboxymethylcellulose) and anion exchangers in the OH− form or bicarbonate form (for example finely milled exchange resin based on styrene-divinylbenzene). In this way, electrolytes formed in an enzyme-catalyzed process are bonded and a deionized medium results.

The chromogen has a high affinity to the cellulose ion exchanger used and is only slightly mobilized by electrolytes.

Hence, buffer systems of relatively low ionic strength can also be added to the reaction zone and detection zone. For example, bipolar buffer substances of a suitable pH value, such as N-morpholino-3-propanesulfonic acid can be used for this purpose.

I claim:

1. A compound selected from the group consisting of compounds of the formula

Polymer—OCH₂CH(OH)CH₂O(CH₂)₄OCH₂CH(OH)CH₂NH—

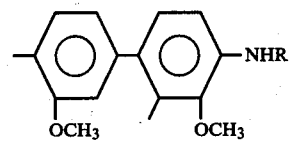

wherein R is H or —CH₂CH₂OH,

Polymer—OCH₂CONH(CH₂)₆NHCO— 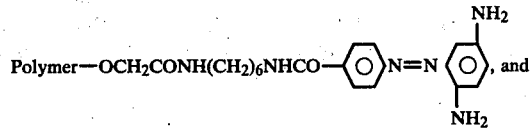, and

Polymer—OCH₂CONHCH₂CH₂NHCOCH₂NH—

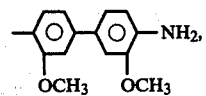

wherein said Polymer is insoluble.

2. A compound as in claim 1 wherein said Polymer is a polymer carrying hydroxyl groups.
3. A compound as in claim 1 wherein said Polymer is cellulose.
4. The compound as in claim 1 of the formula Polymer—OCH₂CH(OH)CH₂O(CH₂)₄OCH₂CH(OH)CH₂NH—

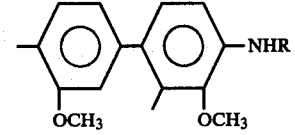

in which R is H or —CH₂CH₂OH.

5. The compound as in claim 4 wherein said Polymer is a polymer carrying hydroxyl groups.
6. The compound as in claim 4 wherein said Polymer is cellulose.
7. A compound as in claim 1 of the formula Polymer-OCH₂CONH(CH₂)₆NHCO 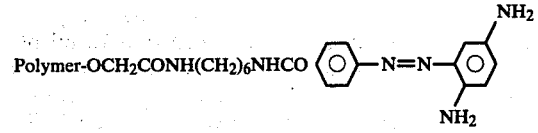

8. The compound as in claim 7 wherein said Polymer is a polymer carrying hydroxyl groups.
9. The compound as in claim 7 wherein said Polymer is cellulose.
10. A compound as in claim 1 of the formula Polymer-OCH₂CONHCH₂CH₂NHCOCH₂NH 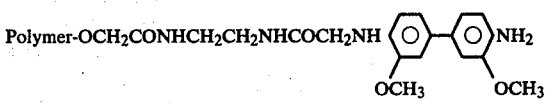

11. The compound as in claim 10 wherein said Polymer is a polymer carrying hydroxyl groups.
12. The compound as in claim 10 wherein said Polymer is cellulose.